United States Patent [19]

Langer, Jr. et al.

[11] 4,147,530
[45] Apr. 3, 1979

[54] REDUCTIONS OF INORGANIC SUBSTRATES WITH CHELATED SODIUM HYDRIDOALUMINATES OR HYDRIDOBORATES

[75] Inventors: Arthur W. Langer, Jr., Watchung, N.J.; William M. Bunting, Baton Rouge, La.

[73] Assignee: Exxon Research & Engineering Co., Florham Park, N.J.

[21] Appl. No.: 849,317

[22] Filed: Nov. 7, 1977

Related U.S. Application Data

[60] Continuation-in-part of Ser. No. 655,891, Feb. 6, 1976, which is a division of Ser. No. 527,648, Nov. 27, 1974, abandoned, which is a continuation-in-part of Ser. No. 504,152, Sep. 9, 1974, abandoned.

[51] Int. Cl.$^2$ .................... C22B 15/12; C22B 23/04
[52] U.S. Cl. ...................................... 75/0.5 A; 75/108
[58] Field of Search ............................ 75/0.5 A, 108

[56] References Cited

U.S. PATENT DOCUMENTS

| 3,428,448 | 2/1969 | Bank et al. | 75/108 |
|---|---|---|---|
| 3,458,586 | 7/1969 | Langer | 260/668 |
| 3,632,658 | 1/1972 | Halasa | 260/665 |
| 3,661,556 | 5/1972 | Jolley et al. | 75/0.5 AA |
| 3,663,318 | 5/1972 | Little et al. | 75/0.5 AA |
| 3,679,398 | 7/1972 | Geus | 75/108 |
| 3,734,963 | 5/1973 | Langer et al. | 260/563 R |
| 3,758,585 | 9/1973 | Bunting et al. | 260/583 P |
| 3,770,423 | 11/1973 | Lores et al. | 75/108 |
| 3,806,520 | 4/1974 | Haar | 260/326.8 |
| 3,852,262 | 12/1974 | Vit et al. | 260/205 |
| 3,933,879 | 1/1976 | Langer et al. | 252/49.7 R |
| 4,088,666 | 5/1978 | Langer et al. | 260/439 R |

*Primary Examiner*—G. Ozaki
*Attorney, Agent, or Firm*—Joseph J. Allocca

[57] ABSTRACT

This invention relates to the use of chelated sodium hydridoaluminates or hydridoborates in hydride reductions of inorganic substrates. Novel or improved reductions are obtained at increased rates or selectivities in hydrocarbon media to recover metals.

17 Claims, No Drawings

REDUCTIONS OF INORGANIC SUBSTRATES WITH CHELATED SODIUM HYDRIDOALUMINATES OR HYDRIDOBORATES

CROSS-REFERENCE TO RELATED APPLICATIONS

This application is a continuation-in-part of Ser. No. 655,891 filed Feb. 6, 1976 which is a division of Ser. No. 527,648 filed Nov. 27, 1974, now abandoned, which is a continuation-in-part of Ser. No. 504,152, now abandoned, filed Sept. 9, 1974.

PRIOR ART

The use of lithium aluminum hydride in ether solvents and sodium borohydride in hydroxylic media for reductions of unsaturated substrates is well known to those skilled in the art. Ether solvents pose a high degree of fire hazard as well as a strong tendency to form explosive peroxides thus limiting their use in many industrial applications. Hydroxylic solvents, such as water or methanol, are also of limited utility as they frequently will either not dissolve the organic substrate to be reduced, or they react with the hydride reducing agent. The present invention is a process for using chelated sodium hydridoaluminates and hydridoborates in hydrocarbon media which overcomes these limitations. Polyamine-chelated sodium compounds have been patented separately by the present inventors (U.S. Pat. No. 3,758,585).

THE PRESENT INVENTION

This invention relates to the use of aliphatic, chelating, tertiary polyamines, tertiary aminoethers or polyethers and sodium hydrido compounds in hydride reductions of organic and inorganic substrates in hydrocarbon media. More particularly, this invention relates to an improved reduction process which utilizes hydrocarbon soluble chelated sodium hydridoaluminates or hydridoborates.

The sodium hydrido compounds of this invention have the formula: $MM'H_mY_n$ wherein M is Na, M' is Al or B, Y is a nonreducing group, m is 1 to 4 and n is 0 to 3. The structure of Y is not critical as long as it is unreactive during the reduction process. For example, Y may be hydrocarbyl, halide, alkoxide, secondary amide, mercaptide, other related groups or mixtures thereof. Hydrocarbyl groups normally include $C_1$–$C_{30}$ alkyl, $C_6$–$C_{30}$ aryl, $C_7$–$C_{30}$ aralkyl, $C_3$–$C_{30}$ naphthenyl, and the like.

Illustrative examples of hydrido compounds include $NaAlH_4$, $NaAlH_3Cl$, $NaAlH_2Br_2$, $NaAlHCl_3$, $NaAlH_3OC_4H_9$, $NaBH_4$, $NaB_2H_7$, $NaBH(C_2H_5)_3$, $NaBH_3C_6H_{13}$, $NaBH_3SCH_3$, $NaBH_3N(CH_3)_2$, $NaBH_3CH_2C_6H_5$, $NaBH_3O$ menthyl, $NaBHClC_2H_5(OC_2H_5)$, $NaAlH[N(C_2H_5)_2]_3$, $NaAlH_2[N(C_3H_7)_2]_2$, $NaAlH_3N(C_{10}H_{21})_2$, $NaAlH_3OC_2H_5$, $NaAlH_2BrC_4H_9$, $NaAlH_2N(C_{10}H_{21})_2OC_2H_5$, $NaAlH_3N(C_6H_{11})_2$, $NaAlHBr(i-C_4H_9)$, $NaAlH_2N(C_2H_5)_2SC_6H_5$, $NaAlH_3SC_8H_{17}$, $NaAlHBrOC_2H_5N(C_{10}H_{21})_2$, $NaAlH_2ISCH_3$, $NaAlH_3OC_6H_5$, $NaAlH_3SC_{20}H_{41}$, $NaAlH_3OC_{20}H_{41}$, $NaAlH_3P(C_6H_{11})_2$ and the like.

Preferred sodium hydridoaluminates and hydridoborates include $NaAlH_4$, $NaAlH_3Cl$, $NaAlH_2Br_2$, $NaAlH(OC_2H_5)_3$, $NaAlH_3N(CH_3)_2$, $NaAlH_3SCH_3$, $AaAlH_2(0-1,1,2,2$-tetramethylpropyl$)_2$, $NaAlH_2(OC^*H(CH_3)C_6H_5)_2$, $NaAlH_3NHC^*H(CH_3)C_6H_5$, $NaAlH_3(O$-menthyl$^*)$, $NaAlH_3(O$-$t$-$C_4H_9)$, $NaAlH_3OC_6H_5$, $NaAlH_3P(C_6H_{11})_2$, $NaBH_4$, $NaBH_3C_2H_5$, $NaBH_2(C_4H_9)_2$, $NaBH(C_2H_5)_3$, $NaBH_3OC_2H_5$, $NaBH_2(OCH_3)_2$, $NaBH_3(OCH_2CH_2OCH_3)$, $NaBH_3SC_6H_5$, $NaBH_3N(CH_3)_2$, $NaBH_3(O$-menthyl$^*)$, $NaBH_3Cl$, $NaBH_3C_6H_5$, and the like, wherein * denotes optical activity.

The most preferred compounds are $NaAlH_4$ and $NaBH_4$.

The chelating agent is a polyfunctional hydrocarbyl Lewis base selected from the group consisting of tertiary polyamines, tertiary aminoethers and chelating polyethers.

The chelating agent has one required functionality in a spatial relationship with the other required functionality(ies) in the molecule such that coordinate bonds are eatablished between the functionalities and the sodium cation of the compound.

The tertiary polyamine or aminoether chelating agent may be sparteine, an N,N'-di-($C_1$–$C_4$ alkyl) bispidin, tris-($\beta$-$C_1$–$C_4$-dialkylaminoethyl)-amine, as well as those compounds falling within the scope of the following general formulas:

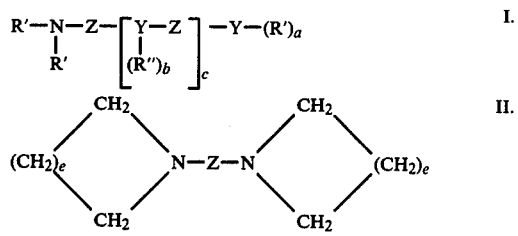

wherein a is 1 or 2, depending on the valence of Y; b is 0 or 1, depending on the valence of Y; c is an integer of 0 to 4, inclusive; e is an integer of 0 to 3, inclusive; R' is the same or different $C_1$–$C_4$ alkyl radical, R" is the same or different $C_1$–$C_4$ alkyl radical or $C_6$–$C_{10}$ aryl or aralkyl radicals; Y is a nitrogen or oxygen atom; and Z is a nonreactive radical selected from the group consisting of (1) $C_4$–$C_{10}$ cycloaliphatic or $C_6$–$C_{10}$ aromatic radicals and their lower alkyl derivatives wherein said radicals are attached to the nitrogen and Y atoms in Formula I and the nitrogen atoms in Formula II at 1,2-positions on the aromatic rings or 1,2- or 1,3-positions on the cycloaliphatic rings; and (2) 2 to 4 methylenic radicals, wherein each methylenic radical contains 0 to 2 monovalent hydrocarbon radicals of 1 to 6 carbon atoms.

Suitable nonlimiting examples of chelating Lewis bases falling within the scope of the above formulas are: N,N,N',N'-tetramethyl-1,2-cyclopentanediamine, N,N,N',N'-tetramethyl-1,2-cyclohexanediamine (cis, trans or mixtures), N,N,N',N'-tetramethyl-o-phenylenediamine, 4-ethyl-N,N,N',-N'-tetramethyl-o-phenylenediamine, N,N,N",N"'-tetramethyl-N'-phenyl diethylene-triamine, N,N,N',N'-tetramethyl-1,2-ethanediamine, N,N,N',N'-tetramethyl-1,3-propanediamine, N,N,N',N",N"-pentamethyl-diethylenetriamine, N,N,N',N'-tetramethyl-1,2-propanediamine, N,N'-dimethyl-N,N'-diethyl-1,2-ethanediamine, N,N,N',N'-tetramethyl-1-cyclohexyl-1,2-ethanediamine, N,N,N',N'-tetramethyl-2,3-butanediamine, N,N,N',N'-tetramethyl-1,4-butanediamine, N,N,N',N",N"',N""-hexamethyl triethylenetetramine, N,N,N',N",N"',N"",N""', N"""-octamethylpentaethylenehexamine, beta-(dimethylamino)ethyl methyl ether, beta-diethylaminoethyl ethyl ether, bis-($\beta$-dimethylaminoethyl) ether, beta-(dimethylamino)-ethyl, ethyl ether, gamma-(dimethylamino)-propyl methyl ether, ortho-dimethylamino anisole; 1,2-dipyrrolidylethane, trans-1,2-dipyrrolidyl cyclohexane, 1,2-dipiperidylethane, 1,3-dipyrrolidylpropane, 1,2-dipyrrolidylpropane, 2,2-dimethyl-1,3-dipyrrolidylpropane, 1,1,1-tris-(pyrrolidylmethyl)-ethane, N,N'-dipropyl-9,9-dimethylbispidin.

The chelating polyethers of this invention have the formula:

R'O—Z—[O—Z]<sub>c</sub>—O—R' wherein Z, R' and c are the same as defined above.

Suitable nonlimiting examples of chelating polyethers falling within the scope of the above formula are: dimethoxyethane (i.e. glyme), diglyme, triglyme, tetraglyme, trans-1,2-dimethoxycyclohexane, 2,6-dioxydecane, 3,7-dioxynonane, diethylcatechol, 2,5,8-trioxydecane, 7-ethyl-2,5,8-trioxydecane, 4-phenyl-2, 5-dioxyhexane, 2,11-dimethyl-4,7,10, 13-tetraoxytetradecane, and the like.

Preferred chelating polyethers include glyme, diglyme, triglyme or tetraglyme.

Particularly preferred, since they generally give rise to hydrocarbon-soluble complexes and are more stable to decomposition, are the tertiary polyamines (i.e. all of the heteroatoms are tertiary nitrogen atoms) containing at least 5 carbon atoms and at least 2 tertiary nitrogen atoms. Particularly preferred species of the chelating tertiary polyamines are N,N,N',N'-tetramethyl-1,2-ethanediamine (TMED), N,N,N',N'-tetramethyl-1,3-propanediamine (TMPD), N,N,N',N'-tetramethyl-1,2-cyclohexanediamine (cis, trans or mixtures) (TMCHD), N,N,N',N'',N''-pentamethyl diethylenetriamine (PMDT), N,N,N',N'',N''',N'''-hexamethyl triethylenetetramine (HMTT), tris-(β-dimethylaminoethyl)amine (iso-HMTT), heptamethyltetraethylenepentamine (HMTP), octamethylpentaethylenehexamine (OMPH) and higher alkyl derivatives thereof such as the corresponding tris-(β-diethylaminoethyl)amine, dipyrrolidylethane, etc.

Not all sodium compounds form complexes with the above-described chelating agents. It is, however, possible to relate success in chelating said compounds to the lattice energy of the unchelated compounds and to find an approximate cutoff lattice energy above which chelation does not occur. This cutoff lattice energy has been experimentally determined to be about 180 kcal/mole for sodium compounds. Since the ability to form chelates is obviously dependent on the chelating agent employed, this cutoff lattice energy is also chelating agent dependent; i.e. only chelating agents capable of forming the most stable complexes will chelate compounds having lattice energies near the upper limits.

The chelated compounds decompose upon heating to give the unchelated compound as a precipitate and free chelating agent in solution. Upon cooling, this reaction is reversible. The temperature at which the uncomplexed salt precipitates is quite sharp (1°–2°) and reproducible. Using this information, it was possible to determine the relative thermal stabilities of the chelated sodium borohydride. Table I, below, contains decomposition temperature for a variety of chelates. These temperatures were obtained by synthesizing the chelates in benzene, filtering the reaction to give a clear solution, and heating the solution in an oil bath at the rate of about 1° C./min. The temperature at which the NaBH<sub>4</sub> precipitates was taken as the decomposition temperature.

TABLE I

| Chelate Decomposition Temperatures | |
|---|---|
| NaBH<sub>4</sub> | Temp. ° C. |
| PMDT | 45 |
| HMTT | 45–46 |
| iso-HMTT | 56–58 |
| HMTP | 50–51 |

From this information, it can be seen that the thermal stabilities are chelating agent dependent; e.g., chelates of iso-HMTT are more stable than those of HMTT, which are more stable than those of PMDT, which in turn are more stable than those of TMED. This same order can be seen for the cutoff lattice energy which, as already stated, is also chelating agent dependent. Table II, below, lists some inorganic sodium compounds in order of increasing lattice energy and the results of attempts to chelate these compounds with iso-HMTT, HMTT and PMDT.

TABLE II

| | Complexation Depends on Lattice Energy | | | | |
|---|---|---|---|---|---|
| | | Complex Formation | | | |
| | Lattice | HMTT | PMDT | Iso-HMTT | |
| Compound | Energy* | Yes | NO | Yes | No |
| NaClO<sub>4</sub> | 159–175 | x | | | |
| NaSCN | 163–178 | x | | | |
| NaI | 164–166 | x | | | |
| NaBH<sub>4</sub> | 168 | x | | x | |
| NaN<sub>3</sub> | 169–175 | | x | x | |
| NaNO<sub>3</sub> | 173–181 | | x | x | |
| NaBr | 176–178 | | x | x | |
| NaCN | 177–185 | | x | | x |
| Na acetate | 182–198 | | x | | |
| NaCl | 185–186 | | x | | |
| NaNO<sub>2</sub> | 185–201 | | x | | |
| NaH | 193–202 | | x | | |
| NaOH | 211 | | x | | |

*Several authors as compiled in M. F. C. Ladd and W. H. Lee in H. Reiss, ed., Progr. Solid State Chem., Vol. I, Pergamon Press, London, 1964.

The complex of the sodium compound may be readily prepared by mixing the selected compound (having the requisite maximum lattice energy) with the selected chelating agent in the absence of solvent. Such mixing may also be accomplished in the presence of inert hydrocarbons, e.g., C<sub>4</sub>–C<sub>20</sub> alkanes (e.g. pentane, heptane, hexadecane; C<sub>6</sub>–C<sub>20</sub> aromatics (e.g. benzene, toluene, xylene, dibutylnaphthalene); halogenated aromatics (e.g. chlorobenzene, dichlorobenzene, heterocyclic compounds (e.g. pyridine, thiophene), or mixtures thereof. The most preferred solvents are aromatics and halogenated aromatics such as benzene, toluene, xylene, chlorobenzene, and the like.

The amount of the diluent is not critical and amounts in the range of 0 to 99.9 wt. percent, based on the chelated compound may be conveniently employed. Thus, the chelate may be formed in the absence of solvents, in the form of pastes and in solutions.

Regardless of the method employed the preparation of the chelate is preferably carried out under anhydrous conditions.

The complex may be readily prepared at temperatures from about −100° C. to about 100° C., preferably 0° to 60° C., the latter temperature range is preferred because of convenience and also since higher temperatures favor dissociation of the less stable complexes. Higher temperatures may be used where chelate stability permits. Pressures may range from subatmospheric to 100 psig or more. For convenience sake, atmospheric pressures are preferred.

The molar ratio of sodium compound to chelating agent is preferably 0.1 to 10, and most preferably 1 to 1. However, it should be understood that the amount of chelating agent employed may influence the structure of the resultant chelate. In this regard, it has been found that true chelate formation occurs only with certain specific ratios; that is, if an incorrect ratio (for true compound formation) were employed, the product would have prodominantly the composition of the nearest true compound and it would consist of a mixture of several compounds. Although 1:1 complexes are preferred, it is within the scope of this invention to prepare and isolate complexes of other stoichiometries such as 1:2 and 2:1.

Of course, the minimum amount of chelating agent should be that stoichiometric amount required to produce the desired type of chelate (where more than one type of chelate is possible from a particular sodium compound and a particular chelating agent). Where only one type of chelate can be formed or where one is not concerned with the particular type of chelate to be formed (assuming that more than one type is possible), it is desirable to employ amounts of chelating agent is excess of the stoichiometric amount.

Suitable unsaturated substrates include compounds having functional groups such as aldehydes, ketones, esters, α, β, unsaturated carbonyl compounds such as RCH=CH—CO$_2$R' or RCH=CH—CONR'$_2$, thioaldehydes, thioketones, imines, oximes, nitriles, hydrazones, semicarbazides, osazones, aroyl and acyl halides, anhydrides and related compounds. Preferred functional groups in the unsaturated substrate are selected from the group consisting of aldehydes, ketones, esters, imines, oximes, anhydrides and hydrazones. Since R' and R'' groups are not critical, some representative, nonlimiting examples are listed for illustrative purposes: benzaldehyde, acetophenone, benzil mono-oxime, butyraldehyde, 2-octanone, octadecyl naphthyl ketone, ethyl cyclohexyl ketone, methyl crotonate, furaldehyde, phenylsulfonylacetone, β-acetylpyridine, thiobenzaldehyde, phenylcyclohexyl thioketone, N-phenylbenzaldimine, phenylacetaldimine, methyl 2-butyl ketoneoxime, ethylpyruvate phenyl hydrazone, glucose phenylosazone, 3-hydroxypropyl methyl ketone, 2-ethoxyethyl methyl ketone, o-dimethylaminobenzaldehyde, 1-ferrocenyl-4-pentanone, CH$_3$SO$_2$CH$_2$CH$_2$COCH$_3$,
(CH$_3$)$_2$PCH$_2$CH$_2$CH$_2$CH$_2$CH(CH$_3$)COC$_2$H$_5$,
ClCH$_2$CH$_2$CH$_2$COCH$_3$, (CH$_3$)$_3$SiCH$_2$CH$_2$COCH$_3$,
(CH$_3$)$_3$SiCOC$_6$H$_5$, (CH$_3$)$_3$GeCH$_2$CH$_2$COCH$_3$,
(CH$_3$)$_3$SnCH$_2$CH$_2$COCH$_3$, C$_6$H$_5$COCO$_2$H,
CH$_3$SCH$_2$CH$_2$COC$_6$H$_5$,
CH$_2$=CHCH$_2$CH$_2$CH$_2$COC$_6$H$_{11}$,
CH≡CCH$_2$CH$_2$COCH(CH$_3$)$_2$,

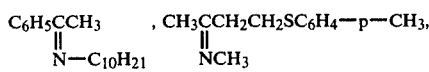

p-ClC$_6$H$_4$CSCH$_3$,

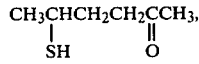

-continued

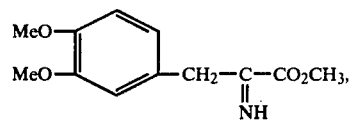

CH$_3$CO$_2$CH$_3$, C$_6$H$_5$CO$_2$C$_4$H$_9$, C$_6$H$_{11}$CO$_2$CH(CH$_3$)$_2$, (CH$_3$CO)$_2$O,

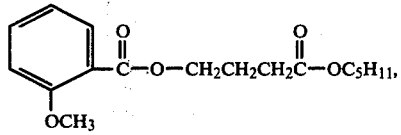

C$_{16}$H$_{33}$CO$_2$CH$_3$, (C$_6$H$_5$CO)$_2$O,

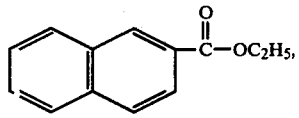

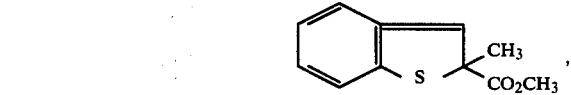

C$_6$H$_5$CH$_2$CO$_2$CH$_3$, C$_6$H$_5$CH$_2$CO$_2$CH$_2$C$_6$H$_5$,

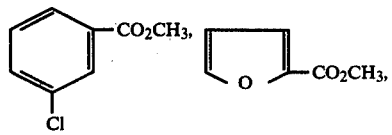

C$_4$H$_9$CO$_2$C(CH$_3$)$_3$, CH$_3$CO$_2$CH$_2$CH$_2$CH$_2$CH$_2$CH$_2$CH$_2$CO$_2$CH$_3$,

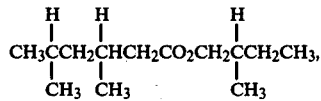

C$_6$H$_5$COCl, CH$_3$COBr, C$_6$H$_5$CN, C$_4$H$_9$CN. Typical reducible inorganic substrates include the salts of the metals of Groups IVB, VB, VIB, VIIB, VIII, IB, IIB, aluminum, gallium, indium, thallium, germanium, tin, lead, antimony, bismuth and uranium, wherein the anion of such salt is selected from the group consisting of Cl, Br, I, F, NO$_3$, CN, SO$_2$, acetate, etc. Suitable nonlimiting examples of reducible inorganic substrates include CuCl[P(C$_6$H$_5$)$_3$]$_2$, Li$_4$Fe(CN)$_6$, AuBr$_3$, AuCl$_3$, Ni(NO$_3$)$_2$, AgNO$_3$, ZnBr$_2$, CdCl$_2$, HgCl$_2$, PdCl$_2$, H$_2$PtCl$_6$, RhCl$_3$, SnCl$_4$, SbCl$_3$, GaCl$_3$, MnO$_2$, CrCl$_3$, TaF$_5$, TiCl$_3$, UF$_6$. Preferred substrates for use with NaBH$_4$ and NaBH$_3$Y include aldehydes, ketones, aroyl halides, acyl halides, thioaldehydes and thioketones.

Any inert hydrocarbon solvent may be used for reaction of the chelated hydrides with unsaturated substrates.

This reaction can be carried out in the presence of any hydrocarbon solvent which is inert to the instant chelated hydrides. For example, aromatic hydrocarbons may be used except in those cases where the complex is reactive enough to metalate aromatic compounds. In those cases, saturated hydrocarbon solvents are preferred. The reaction can be run at any convenient temperature, i.e. from −100° to +200° C. but generally lower temperatures, ranging from −80° to 60° C. are preferred and most preferred is 0°–35° C. The upper temperature is usually limited by the stability of complex.

The mole ratio of the chelate to the unsaturated substrate may be in the range of 10:1 to 1:10, preferably 2:1 to 1:2 and most preferably about 1:1 based on the number of hydride functionalities needed to effect reduction.

Pressure is not critical. The reaction can be run at any convenient pressure ranging from subatmospheric to 100 atmospheres, but pressures ranging from 1–10 atmospheres are preferred and most preferred is a pressure of one atmosphere.

A particularly interesting feature of this invention is the ability to achieve novel or improved reductions at increased rates or selectivities in hydrocarbon media. Thus, for example, sodium aluminum hydride does not reduce benzonitrile in benzene, but PMDT•NaAlH$_4$ in benzene reduces benzonitrile to benzylamine virtually quantitatively in 15 min. at 25° C. Further, often the chelating agent can be used catalytically (i.e. fewer moles of chelating agent than metal hydride). In benzene at 25° C., chelated sodium aluminum hydride reduces aldehydes, ketones, acid halides, aromatic nitriles, organohalides, amides, and nitro compounds. Under similar reaction conditions, chelated sodium borohydride reduces aldehydes quite rapidly, but ketones slowly. Other advantages will become evident from the examples.

EXAMPLE 1

To 0.57 g (15 mmoles) of sodium borohydride were added 50 ml benzene and 5 ml (15 mmoles) HMTT. The reaction was stirred and filtered to give a solid (0.37 g). To the clear solution was added 0.69 g (8 mmoles) of 3-pentanone. The reaction was stirred at 25° C. for 30 min. and a 0.5 ml aliquot of the reaction solution was removed and hydrolyzed (1N HCl). The organic layer was separated and dried twice (K$_2$CO$_3$, MgSO$_4$). The infrared spectrum showed that some of the 3-pentanone had been reduced to 3-pentanol.

EXAMPLE 2

To 0.65 g (12 mmoles) of sodium aluminum hydride were added 25 ml benzene and 1.55 g (15 mmoles) of benzonitrile. The reaction was stirred 1 hr. and an aliquot taken and hydrolyzed. The organic layer was separated and dried. Analysis by gas chromatography showed no reduction of the benzonitrile to benzylamine. This experiment was repeated except that 12 mmoles of PMDT were added prior to the benzonitrile addition. Analysis of the reaction after 1 hr. by gas chromatography showed the conversion of benzonitrile to benzylamine to be 95%. This example demonstrates that chelated sodium aluminum hydride may show greatly increased reactivity in hydrocarbon media compared to unchelated sodium aluminum hydride.

EXAMPLE 3

To 0.65 g (12 mmoles) of sodium aluminum hydride were added 25 ml benzene and 1.55 g (15 mmols) of benzonitrile. After 15 min. reaction time gas chromatography showed that the benzonitrile had not been reduced. A catalytic quantity (1.2 mmoles) of PMDT was then added. After 15 min. benzylamine, but not benzonitrile, was detected in the reaction mixture (G-C analysis). This example shows the greatly increased reactivity of chelated sodium aluminum hydride over unchelated sodium aluminum hydride in benzene and also that the chelating agent may be used catalytically.

EXAMPLE 4

To 0.65 g (12 mmoles) of sodium aluminum hydride were added 25 ml of benzene and 2.6 ml (~24 mmoles) of TMED. After briefly stirring the reaction, 1.55 g (15 mmoles) of benzonitrile was added. At the end of a 1 hr. reaction time, gas chromatography showed conversion of benzonitrile to benzylamine to be 85%. In this example, the ratio of chelating agent to metal hydride was 2:1.

EXAMPLE 5

To 0.65 g (12 mmoles) of sodium aluminum hydride were added 25 ml of benzene, 1 ml (~12 mmoles) of tetrahydrofuran, and 1.55 g (15 mmoles) of benzonitrile. There was no detectable (GC) reduction of the benzonitrile to benzylamine in a 1 hr. reaction time at 25° C. Similar results were obtained when 36 mmoles of tetrahydrofuran were used in the above experiment. When the tetrahydrofuran in the above experiment was replaced by 12 mmoles of triglyme, reduction of the benzonitrile to benzylamine was 85% complete at the end of a 15 min. reaction period at 25° C. This example shows that monoethers such as tetrahydrofuran cannot be used to replace the chelating amines, but that the chelating polyethers are satisfactory substitutes for the chelating polyamines.

EXAMPLE 6

To 0.65 g (12 mmoles) of sodium aluminum hydride and 1.6 g (12 mmoles) of diglyme in 25 ml of benzene was added 2.58 g (30 mmoles) of diethyl ketone. The diethyl ketone was determined by gas chromatography to be reduced to 3-pentanol in 74% yield in a 15 min. reaction time.

EXAMPLE 7

The reactions of this example were run using PMDT•NaAlH$_4$ in a procedure similar to Example 2 and at 25° C. in benzene.

| Compound | R$^a$ | Time (min) | Product | Yield |
| --- | --- | --- | --- | --- |
| benzonitrile | 1.25 | 15 | benzylamine | 95 |
| benzaldehyde | 2.5 | 60 | benzylalcohol | 85 |
| diethyl ketone | 2.5 | 15 | 3-pentanol | 95 |
| acetophenone | 2.5 | 15 | 1-phenylethanol | 95 |
| 1-bromooctane | 2.5 | 60 | octane | 50 |

$^a$Molar ratio of organic compound to metal hydride.

EXAMPLE 8

The reactions of this example were run using PMDT•NaBH$_4$ in a procedure similar to Example 2 at 25° C. in benzene.

| Compound | R$^a$ | Time (min) | Product | Yield |
| --- | --- | --- | --- | --- |
| benzaldehyde | 3.3 | 60 | benzylalcohol | 70 |
| diethyl ketone | 2.5 | 60 | 3-pentanol | 25 |
| acetophenone | 2.5 | 60 | 1-phenylethanol | 11 |

$^a$Molar ratio of organic compound to metal hydride.

EXAMPLE 9

To 1.0 g (5 mmoles) of cuprous iodide were added 25 ml of benzene and 1.1 ml (5 mmoles) of PMDT. This reaction mixture was stirred 1 hr. and added to a second reaction mixture consisting of 0.16 g (3 mmoles) of sodium aluminum hydride, 10 ml of benzene and 0.9 ml of iso-HMTT. A gas was slowly evolved and the reaction turned reddish-brown and finally black showing that copper (I) was reduced to copper (O).

EXAMPLE 10

A partial solution (green) of 0.74 g (1 mmole) of bis (triphenylphosphine) nickel (II) bromide in 10 ml of toluene was added to 0.05 g (1 mmole) of sodium aluminum hydride and 0.3 ml (1 mmole) of iso-HMTT in 10 ml of toluene. The reaction color changed from green to brown-black showing that nickel (II) had been reduced to nickel (O).

EXAMPLE 11

Following the procedure of Example 2, (TMEDA)$_2$NaAlH$_4$ was prepared in benzene and reacted for one hour with benzonitrile at 25° C. Benzylamine was obtained in 85% yield.

EXAMPLE 12

To 0.65 g (12 mmoles) of NaAlH$_4$ in 25 ml of benzene was added 2.08 g (30 mmoles) of triglyme and 1.55 g (12 mmoles) of benzonitrile. The reaction mixture was stirred at room temperature under nitrogen for 15 minutes. The reaction mixture was hydrolyzed and the organic phase was analyzed by gas chromatography. An 85% yield of benzylamine was obtained. This reaction demonstrates that polyether chelated sodium hydridoaluminates may be used in hydrocarbon media for reduction of unsaturated substrates. Activity was lower than with the corresponding triamine (PMDT) in Example 7.

EXAMPLE 13

25 mmoles of PMDT and 25 mmoles of NaAlH$_4$ were added to 50 ml of benzene and the mixture was stirred for 18 hours and was then filtered. The filtrate was evaporated under vacuum yielding crystalline PMDT•NaAlH$_4$. An 8 mmole portion of the PMDT•NaAlH$_4$ was dispersed in 25 ml of n-heptane and 8 mmoles of benzonitrile was added with stirring An immediate exothermic reaction occurred and after one hour a portion of the reaction mixture was hydrolyzed with 10% NaOH solution. The organic phase of the hydrolyzed product was analyzed by vapor phase chromatography. It was found that reduction of the benzonitrile had occurred. This illustrates that the complexes are effective reducing agents even when used as slurries in poor solvents.

What is claimed is:

1. A process for reducing inorganic substrates which comprises the step of reacting a reducible inorganic substrate with a chelate compound, said chelate compound formed by mixing a sodium hydrido compound and a chelating polyfunctional hydrocarbyl Lewis base in an inert hydrocarbon medium at −100° to +200° C., and recovering metals.

2. The process according to claim 1 wherein the sodium hydrido compound is of the formula MM'H$_m$Y$_n$, wherein M is Na, M' is Al or B; m is 1 to 4 and n is 0 to 3; Y is a nonreducing, unreactive group.

3. The process according to claim 1 wherein the chelate compound is tetramethylcyclohexanediamine•-NaAlH$_4$.

4. The process according to claim 1 wherein the chelate compound is tetramethylethanediamine•-NaAlH$_4$.

5. The process according to claim 1 wherein the chelate compound is pentamethyldiethylenetriamine•-NaBH$_4$.

6. The process according to claim 1 wherein the chelate compound is tetramethylethanediamine•-NaBH$_4$.

7. The process according to claim 1 wherein the sodium hydrido compound is NaAlH$_4$.

8. The process according to claim 1 wherein the sodium hydrido compound is NaBH$_4$.

9. The process according to claim 1 wherein the chelating polyfunctional hydrocarbyl Lewis base is selected from the group consisting of tertiary polyamines, tertiary aminoethers, chelating polyethers, sparteine, N,N'-di-(C$_1$-C$_4$ alkyl) bispidin, tris-(β-C$_1$-C$_4$-dialkylaminoethyl)-amine and those compounds having the formulas:

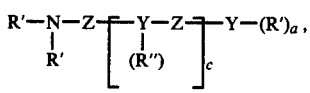

I

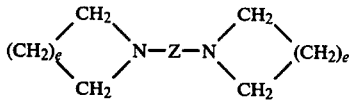

II

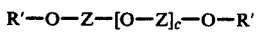

III wherein a is 1 or 2, depending on the valence of Y; b is 0 or 1, depending on the valence of Y; c is an integer of 0 to 4 inclusive; e is an integer of 0 to 3 inclusive; R' is the same or different C$_1$-C$_4$ alkyl radical, R" is one selected from the group consisting of C$_1$-C$_4$ alkyl, C$_6$-C$_{10}$ aryl or aralkyl radical; Y is a nitrogen or oxygen atom; Z is a nonreactive radical selected from the group consisting of:

(1) C$_4$-C$_{10}$ cycloaliphatic or C$_6$-C$_{10}$ aromatic radicals and their lower alkyl derivatives wherein said radicals are attached to the nitrogen and Y atoms is Formula I, the nitrogen atoms in Formula II and the oxygen atoms in Formula III at 1,2-positions on the aromatic rings or 1,2- or 1,3- positions on the cycloaliphatic rings; and (2) 2 to 4 methylenic radicals, wherein each methylenic radical contains 0 to 2 monovalent hydrocarbon radicals of 1 to 6 carbon atoms.

10. The process according to claim 1 wherein the chelating polyfunctional hydrocarbyl Lewis base is a chelating polyether of the formula:

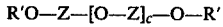

wherein c is an integer of from 0 to 4 inclusive, Z is a nonreactive radical selected from the group consisting of (1) C$_4$-C$_{10}$ cycloaliphatic or C$_6$-C$_{10}$ aromatic radicals and their lower alkyl derivatives wherein said radicals are attached to the oxygen atoms at 1,2-positions on the aromatic rings or 1,2- or 1,3 positions on the cycloaliphatic rings and (2) 2 to 4 methylene radicals wherein each methylene radical contains 0 to 2 monovalent hydrocarbon radicals of 1 to 6 carbon atoms;

and R' is the same or different $C_1$-$C_4$ alkyl radical.

11. The process according to claim 10 wherein the chelating polyfunctional hydrocarbyl Lewis base is glyme.

12. The process according to claim 10 wherein the chelating polyfunctional hydrocarbyl Lewis base is diglyme.

13. The process according to claim 10 wherein the chelating polyfunctional hydrocarbyl Lewis base is triglyme.

14. The process according to claim 10 wherein the chelating polyfunctional hydrocarbyl Lewis base is tetraglyme.

15. The process according to claim 14 wherein the inert hydrocarbon medium is an aromatic.

16. The process according to claim 1 wherein the inert hydrocarbon medium is a halogenated aromatic.

17. The process according to claim 1 wherein the Lewis base is a chelating tertiary polyamine.

* * * * *